United States Patent [19]

Nakayama et al.

[11] Patent Number: 5,619,290
[45] Date of Patent: Apr. 8, 1997

[54] PHASE-CONTRAST HAPLOSCOPE AND ROTARY DISC FOR USE THEREWITH

[75] Inventors: Shigekatsu Nakayama, Houya; Seiji Ishimaru, Wakou, both of Japan

[73] Assignee: Tagawa Denki Kenkyusyo Company, Bunkyou-ku, Japan

[21] Appl. No.: 381,781

[22] Filed: Jan. 31, 1995

[30] Foreign Application Priority Data

Feb. 10, 1994 [JP] Japan .................................. 6-016072
Oct. 3, 1994 [JP] Japan .................................. 6-238901

[51] Int. Cl.$^6$ .................................. A61B 3/10; A61B 3/00
[52] U.S. Cl. .......................... 351/217; 351/245; 351/246
[58] Field of Search ................................. 351/205, 201, 351/200, 216, 217, 234, 235, 233, 245, 246

[56] References Cited

U.S. PATENT DOCUMENTS 2,882,789  4/1959  Wilson .................................. 351/217

*Primary Examiner*—Hung X. Dang
*Attorney, Agent, or Firm*—Jordan and Hamburg

[57] ABSTRACT

A haploscope has a housing defining left and right viewing apertures disposed to permit substantial alignment with a subject's left and right eyes and permit viewing through the housing. Projection light sources for projection of left and right images are provided and the housing defines first and second light source apertures for transmission of light from the sources therethrough. The haploscope has first and second projection devices for projecting images using the light passing through respective ones of the first and second light source apertures. The housing has a rotary disc and a motor for rotating the rotary disk within the housing at a position permitting occlusion of the first and second light source apertures and the left and right viewing apertures. The rotary disc has at least one viewing aperture disposed to align with the left and right viewing apertures during rotation of the rotary disc such that only one of the left and right viewing apertures is not occluded at a given time. The rotary disc also has first and second light source transmission apertures disposed to align with respective ones of the light source apertures during rotation of the rotary disc to permit transmission of light therethrough coincident with non-occlusion of respective ones of the left and right viewing apertures.

27 Claims, 11 Drawing Sheets

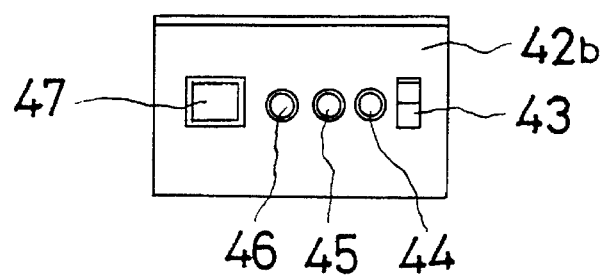
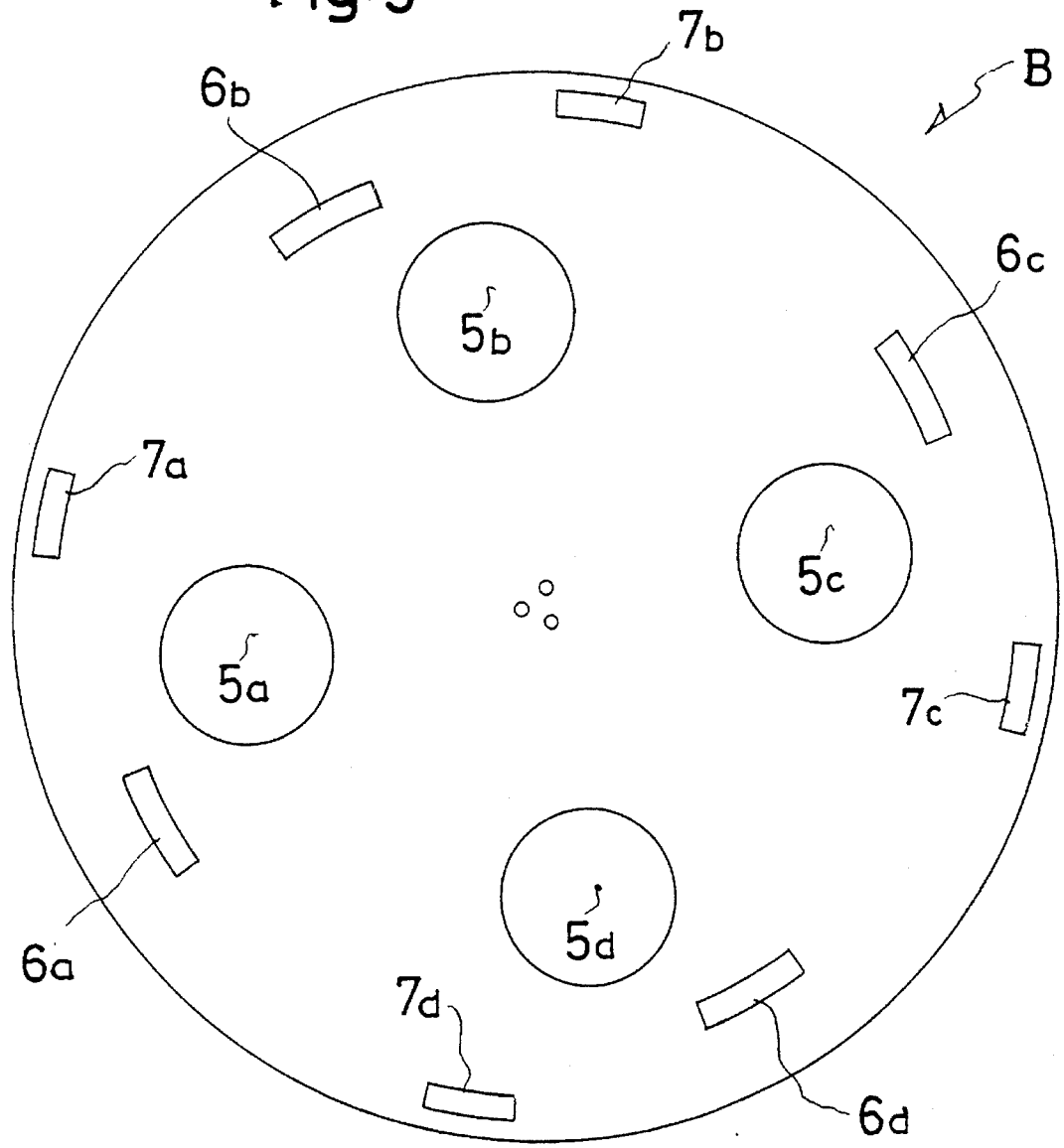

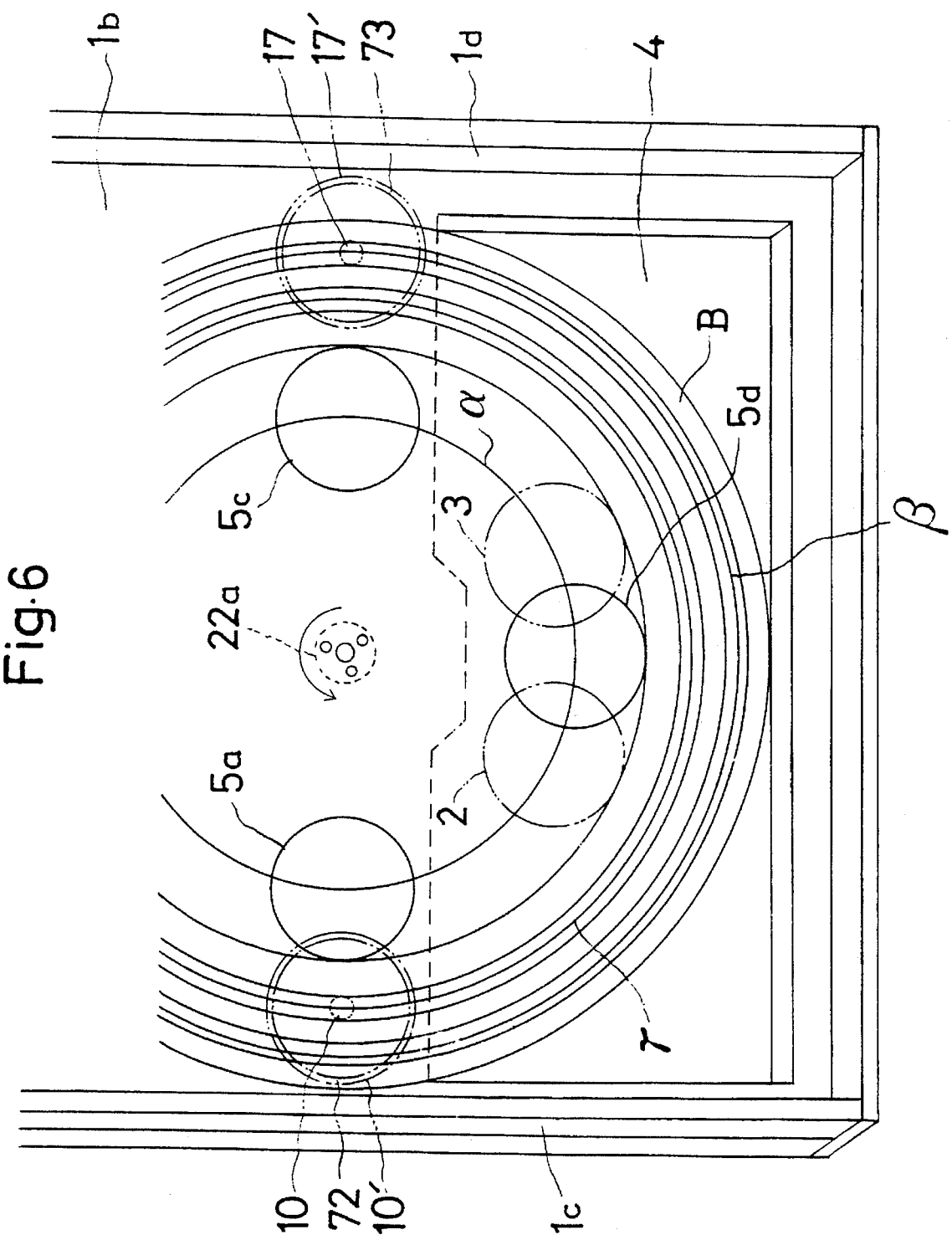

PHASE-CONTRAST HAPLOSCOPE AND ROTARY DISC FOR USE THEREWITH

BACKGROUND OF THE INVENTION

The present invention relates to a phase-contrast haploscope used to examine various functions of binocular vision, i.e. subjective angle of squint, retinal correspondence, fusion faculty, subjective vision, suppression, aniseikonia, circumflex deviation and others, by separating images of right and left eyes in environment most similar to ordinary vision.

According to The Medical Dictionary issued by Nanzando Co., Ltd., a haploscope is an optic axis measuring instrument, which forms images of two separate targets which are similar to or identical to each other on both eyegrounds using a prism or reflecting mirror for uniting the images by the capability of binocular vision and examines fusion power, fusional motion, and the relation between adaptation control and convergence from the capability of binocular vision.

As shown in FIG. 12, in a conventional synchronous type phase-contrast haploscope which has been practically used, targets g, h of eyes are separated by using a pair of sectors a, b which correspond to right and left eyes and which rotate at a high speed in front of eyes with an inter-hole phase difference of 90 degrees and a pair of right- and left-hand projectors e, f having sectors c, d which are synchronized with the sectors a, b, respectively (an image projected by the right-hand projector e is seen only by the right eye, and an image projected by the left-hand projector f is seen only by the left eye). In the FIGS., i to l denote rotating motors, m denotes the plane of projection, n and o denote left- and right-hand lantern slides, p denotes an examinee, and q and r denote left- and right-hand projecting beams.

Because of a rotating speed (100–120 c/s) higher than a critical fusion frequency, in a subjective sense, both targets g, h are recognized continuously and concurrently. By using such apparatus, it is possible to examine said various functions of binocular vision under conditions quite similar to ordinary vision.

On the other hand, there exists a liquid crystal phase-contrast haploscope. The flashing frequency of an image can range from 0.1 to 50 c/s by using liquid crystal shutters which are synchronized with changeover shutters for both eyes. Also, the liquid crystal shutter has an opening/closing characteristic which provides an operation speed up to 50 c/s with a rise/fall time of 5 ms.

SUMMARY OF THE INVENTION

In said conventional synchronous type phase-contrast haploscope, however, it is necessary to synchronously drive expensive rotating motors i–l corresponding to a total of four sectors a–d, i.e. a pair of sectors a, b corresponding to right and left eyes and a pair of sectors c, d corresponding to projectors e, f. This is technically difficult to achieve, and a repeated use over a long period of time causes an out-of-step, condition which is fatal in use. Hence, adjustment for synchronization is needed on occurrence of the out-of-step condition. This is quite troublesome.

On the other hand, in the conventional liquid crystal phase-contrast haploscope, a group of changeover switches must be turned on/off at a high speed for synchronously changing a total of four shutters, i.e. a pair of changeover shutters corresponding to left and right eyes and left- and right-hand liquid crystal shutters. As a result, a chattering phenomenon occurs, causing the mechanical service life of the group of changeover switches to shorten and the frequency of fault occurrence to increase. Moreover, there is a limit to high-speed changeover, and changeover noise occurs frequently. In view of the foregoing, major objects of the present invention to be achieved are described below.

A first object of the present invention is to provide a rotary disc for use with a phase-contrast haploscope which is compact, small-scaled and smaller in the number of parts and to provide such a phase-contrast haploscope.

A second object of the present invention is to provide a rotary disc for use with a phase-contrast haploscope which uses a single motor for high-speed changeover without synchronizing a driving portion and to provide such a phase-contrast haploscope.

A third object of the present invention is to provide a rotary disc for use with a phase-contrast haploscope which operates quietly and is highly durable and to provide such a phase-contrast haploscope.

A fourth object of the present invention is to provide a phase-contrast haploscope which is mobile. A fifth object of the present invention is to provide a phase-contrast haploscope in which the vertical position can be set according to the sitting height of an examinee.

A sixth object of the present invention is to provide a phase-contrast haploscope in which a face setting position can be adjusted according to an individual difference in face profile irrespective of age or sex of examinees.

A seventh object of the present invention is to provide a phase-contrast haploscope in which the size of left- and right-hand targets projected on a plane of projection can be changed.

An eighth object of the present invention is to provide a phase-contrast haploscope in which left- and right-hand targets projected on a plane of projection can be moved vertically and horizontally.

A ninth object of the present invention is to provide a phase-contrast haploscope in which the rotational speed of a driving motor and left- and right-hand illuminances can be regulated.

A tenth object of the present invention is to provide a phase-contrast haploscope in which optical fibers and transmitting optical fibers can be run and arranged neatly.

Other objectives of the present invention will be apparent from the specification, drawings, and particularly from the scope of the appended claims.

The above-described objects are achieved by the following novel features of the present invention.

In the first aspect of the present invention, there is provided a rotary disc for a phase-contrast haploscope which is driven by a motor and which is rotatably mounted on a stationary front plate having a pair of left- and right-hand look-through holes formed therein at positions facing both left and right eyes, leaving a predetermined clearance between the rotary disc and the front plate, wherein through holes which sweep out a concentric circular path and pass in front of said left- and right-hand look-through holes in sequence at a high rotational speed in such a manner as to instantaneously coincide with the look-through holes are formed on the concentric circular path, project-through holes are formed on a concentric circular path having a different diameter from that of said through holes at corresponding positions, each of said project-through holes allowing the passage of a projecting beam for projecting a target which is seen through said left-hand look-through hole and said through hole when the left-hand look-through hole and the through hole coincide with each other, and on the other hand, project-through holes are formed on a concentric circular path having a different diameter from those of said through holes and said project-through holes at corresponding positions, said project-through hole allowing the passage of a projecting beam for projecting a target which is seen through said right-hand look-through hole and said through hole when the right-hand look-through hole and the through hole coincide with each other.

In the second aspect of the present invention, there is provided a rotary disc for a phase-contrast haploscope, wherein the through holes and the project-through holes in the first aspect are formed on respective concentric circular paths spaced equally.

In the third aspect of the present invention, there is provided a rotary disc for a phase-contrast haploscope, wherein the through holes and the project-through holes in the first aspect are respectively arranged with an inter-hole phase difference of 90 degrees in a circumferential direction.

In the fourth aspect of the present invention, there is provided a rotary disc for a phase-contrast haploscope, wherein the left- and right-hand look-through holes and the through holes in the first or second aspect are shaped in a large circle having the same size, and the project-through holes are shaped in a rectangular arc.

In the fifth aspect of the present invention, there is provided a rotary disc for a phase-contrast haploscope, wherein the target in the first, second, third or fourth aspect comprises a character, a graphic pattern, a symbol or a combination thereof, or other images.

In the sixth aspect of the present invention, there is provided a phase-contrast haploscope which includes a disc case which has a front plate having a pair of left- and right-hand look-through holes in its lower half portion and a rear plate having a through window or left- and right-hand through holes formed in its lower half portion, wherein a pair of left- and right-hand beam emitting holes and beam incident holes corresponding to the left- and right-hand look-through holes are formed respectively in the front plate and in the rear plate at desired opposed positions, and which contains a motor driven rotary disc in a rotatable manner, the rotary disc having through holes and project-through holes formed therein, the through holes and project-through holes sweeping out respective concentric circular paths of different diameters and passing at a high rotational speed between said left- and right-hand look-through holes and said through window or left- and right-hand through holes, opposed to each other, and between said left- and right-hand beam emitting holes and left- and right-hand beam incident holes, opposed to each other, in such a manner as to instantaneously coincide with corresponding holes and the window, and left- and right-hand projectors into which slide loaders allowing a slide to be inserted thereinto and removed therefrom are incorporated and which takes in beams from said beam incident holes, irradiates the slides with the beams through appropriate beam transmitting means and projects projecting beams having passed through onto the plane of projection.

In the seventh aspect of the present invention, there is provided a phase-contrast haploscope, wherein the disc case and projectors in the sixth aspect are mounted on a base which is raised and lowered for positioning.

In the eighth aspect of the present invention, there is provided a phase-contrast haploscope, wherein the disc case in the seventh aspect is mounted on a gantry stand or left- and right-hand parallel support stands standing on the base, which left- and right-hand parallel support stands are accompanied by left- and right-hand parallel guide uprights standing in front of them.

In the ninth aspect of the present invention, there is provided a phase-contrast haploscope, wherein the base in the seventh or eighth aspect is supported on a mobile lifter support.

In the tenth aspect of the present invention, there is provided a phase-contrast haploscope, wherein the front plate in the sixth, seventh, eighth or ninth aspect is provided with a forehead rest fixed to the end of a slide rod which is slidably inserted into a guide cylinder for positioning and adjustment, and the guide cylinder is mounted on the front plate above the middle between the left- and right-hand look-through holes.

In the eleventh aspect of the present invention, there is provided a phase-contrast haploscope, wherein the left- and right-hand look-through holes in the sixth, seventh, eighth, ninth or tenth aspect are provided with transparent plates which are attached thereto by appropriate means.

In the twelfth aspect of the present invention, there is provided a phase-contrast haploscope, wherein the left- and right-hand beam emitting holes in the sixth, seventh, eighth, ninth, tenth or eleventh aspect are provided with connectors which are attached to their outer ends, and the beam emitting ends of the left- and right-hand optical fibers, which are respectively connected to light source boxes fixed to the lower surface of the base at the lateral sides thereof in a hanging manner, are allowed to be inserted into and fixed to the connectors.

In the thirteenth aspect of the present invention, there is provided a phase-contrast haploscope, wherein the left- and right-hand beam emitting holes in the sixth, seventh, eighth, ninth, tenth or eleventh aspect are provided with sockets which are connected with a power cord and into which halogen lamps are screwed.

In the fourteenth aspect of the present invention, there is provided a phase-contrast haploscope, wherein the left- and right-hand beam incident holes in the sixth, seventh, eighth, ninth, tenth, eleventh, twelfth or thirteenth aspect are provided with connectors which are attached to their outer ends, and the beam incident ends of left- and right-hand transmitting optical fibers are allowed to be inserted into and fixed to the connectors.

In the fifteenth aspect of the present invention, there is provided a phase-contrast haploscope, wherein the rear plate in the sixth, seventh, eighth, ninth, tenth, eleventh, twelfth, thirteenth or fourteenth is provided with a motor which is mounted on its outer face, and a motor shaft to which the rotary disc is attached penetrates the rear plate inwardly.

In the sixteenth aspect of the present invention, there is provided a phase-contrast haploscope, wherein the base in the sixth, seventh, eighth, ninth, tenth, eleventh, twelfth, thirteenth, fourteenth or fifteenth aspect is provided with a control box which is attached to its one end in a hanging manner.

In the seventeen aspect of the present invention, there is provided a phase-contrast haploscope, wherein the left- and right-hand projectors in the sixth, seventh, eighth, ninth, tenth, eleventh, twelfth, thirteenth, fourteenth, fifteenth or sixteenth aspect are provided with zooms which are integrally incorporated into the forward ends of the projectors.

In the eighteenth aspect of the present invention, there is provided a phase-contrast haploscope, wherein the left- and right-hand projectors in the sixth, seventh, eighth, ninth, tenth, eleventh, twelfth, thirteenth, fourteenth, fifteenth, sixteenth or seventeenth aspect are provided with connectors which are integrally incorporated into the rear ends of the projectors, and the beam irradiating ends of the left- and right-hand transmitting optical fibers are allowed to be inserted into and fixed to the connectors.

In the nineteenth aspect of the present invention, there is provided a phase-contrast haploscope, wherein each of the left- and right-hand projectors in the sixth, seventh, eighth, ninth, tenth, eleventh, twelfth, thirteenth, fourteenth, fifteenth, sixteenth, seventeenth or eighteenth aspect, is pivoted between forked brackets in such a manner that a vertical angle is adjustable using operating means of the forked brackets, which forked brackets are mounted on the top ends of left- and right-hand support stands standing on the base in such a manner as to be horizontally swingable using the operating means.

In the twentieth aspect of the present invention, there is provided a phase-contrast haploscope, wherein the operating means in the nineteenth aspect, includes an equilibrating tension spring one end of which is attached to the front end of an auxiliary plate attached to the bottom side of a projector and the other end of which is attached to a forked bracket base coupling portion, thereby always giving the behavior of lying down, and a handle which is attached to the rear end of the auxiliary plate and extends downward at right angles.

In the twenty-first aspect of the present invention, there is provided a phase-contrast haploscope, wherein the left- and right-hand projectors in the sixth, seventh, eighth, ninth, tenth, eleventh, twelfth, thirteenth, fourteenth, fifteenth, sixteenth, seventeenth or eighteen aspect upward penetrate the base with a predetermined spacing.

In the twenty-second aspect of the present invention, there is provided a phase-contrast haploscope, wherein the left- and right-hand projectors in the sixth, seventh, eighth, ninth, tenth, eleventh, twelfth, thirteenth, fourteenth, fifteenth, sixteenth, seventeenth, eighteenth or twenty-first aspect include left- and right-hand seat rings which are rotatably mounted on the top ends of the projectors in such a manner as to cover left- and right-hand zooms, forked brackets which stand on the left- and right-hand seat rings in such a manner as to swing horizontally together with the seat rings by operation with operating means for horizontal and vertical swing movement, and left- and right-hand mirrors which are pivoted between forked brackets in such a manner that a vertical angle is adjustable using the operating means for horizontal and vertical swing movement and as to face the top ends of the left- and right-hand zooms.

In the twenty-third aspect of the present invention, there is provided a phase-contrast haploscope, wherein the operating means for horizontal and vertical swing movement in the twenty-second aspect is a pair of left- and right-hand right-angle handles which are fixed to the inner sides of the left- and right-hand arms which obliquely downward project from and are located at the middle portions of the back sides of the left- and right-hand mirrors.

In the twenty-fourth aspect of the present invention, there is provided a phase-contrast haploscope, wherein the gantry stand in the sixth, seventh, eighth, ninth, tenth, eleventh, twelfth, thirteenth, fourteenth, fifteenth, sixteenth, seventeenth, eighteenth or nineteenth aspect include a chin rest which is fixed in a manner capable of rising or lowering for positioning to the end portion of a crank bracket, whose base end is fixed on the bottom face of the top plate of the gantry stand below the middle between the left- and right-hand look-through holes.

In the twenty-fifth aspect of the present invention, there is provided a phase-contrast haploscope, wherein the left- and right-hand parallel guide uprights in the sixth, seventh, eighth, ninth, tenth, eleventh, twelfth, thirteenth, fourteenth, fifteenth, sixteenth, seventeenth, eighteenth, nineteenth, twenties or twenty-first aspect include a cross-plate which bears a chin rest at its central portion corresponding to the middle between the left- and right-hand look-through holes and which stretches between the left- and right-hand parallel guide uprights in such a manner that its both ends can slide up and down along the parallel guide uprights for positioning.

In the twenty-sixth aspect of the present invention, there is provided a phase-contrast haploscope, wherein the intermediate portions of left- and right-hand optical fibers and left- and right-hand transmitting optical fibers in the sixth, seventh, eighth, ninth, tenth, eleventh, twelfth, thirteenth, fourteenth, fifteenth, sixteenth, seventeenth, eighteenth, nineteenth, twenties or twenty-fourth aspect pass through left- and right-hand auxiliary cases which stand on the gantry stand on both sides thereof so as to support the sides of the disc case, and the intermediate portions of the left- and right-hand optical fibers also pass through the left- and right-hand supports of the gantry stand.

In the twenty-seventh aspect of the present invention, there is provided a phase-contrast haploscope, wherein the intermediate portions of the left- and right-hand optical fibers and left- and right-hand transmitting optical fibers in the sixth, seventh, eighth, ninth, tenth, eleventh, twelfth, thirteenth, fourteenth, fifteenth, sixteenth, seventeenth, eighteenth, nineteenth, twenties, twenty-first, twenty-second, twenty-third or twenty-fifth aspect pass through the left- and right-hand support stands.

In the present invention having the above-described novel means, a single rotary disc is used to change over left- and right-hand targets projected on a plane of projection corresponding to left- and right-hand look-through holes synchronously with the changeover of the left- and right-hand look-through holes. As a result, apparatus according to the present invention is compact, small-scaled, and mobile to any location provided with a power source and does not occupy much space.

Moreover, a base can be raised and lowered. In addition, the apparatus is adjustable to meet the physique and face profile of an examinee by adjusting; the position of a forehead rest and chin rest. Hence, a common apparatus can be used for examination irrespective of age or sex.

Various kinds of examinations can be securely performed by regulating the changeover speed of the synchronized left- and right-hand look-through holes and left- and right-hand projected targets by changing a motor speed from a control panel on a control box and thus increasing/decreasing the number of revolutions of a rotary disc, by individually adjusting the illuminance of the left- and right-hand projected targets, by zooming left- and right-hand projectors to individually zoom out or in the left- and right-hand projected targets, and by swinging horizontally the left- and right-hand projectors and mirrors and adjusting the vertical angle thereof to individually move the left- and right-hand projected targets.

BRIEF DESCRIPTION OF THE DRAWINGS

FIG. 4 is an enlarged plan view showing a control box of the haploscope according to the first embodiment;

FIG. 5 is an enlarged front view showing an embodiment of a rotary disc according to the present invention;

FIG. 6 is a partially omitted perspective front view showing a disc case with its front plate removed;

DETAILED DESCRIPTION OF THE INVENTION

A first embodiment of the present invention will be described with reference to drawings.

Figure 1:
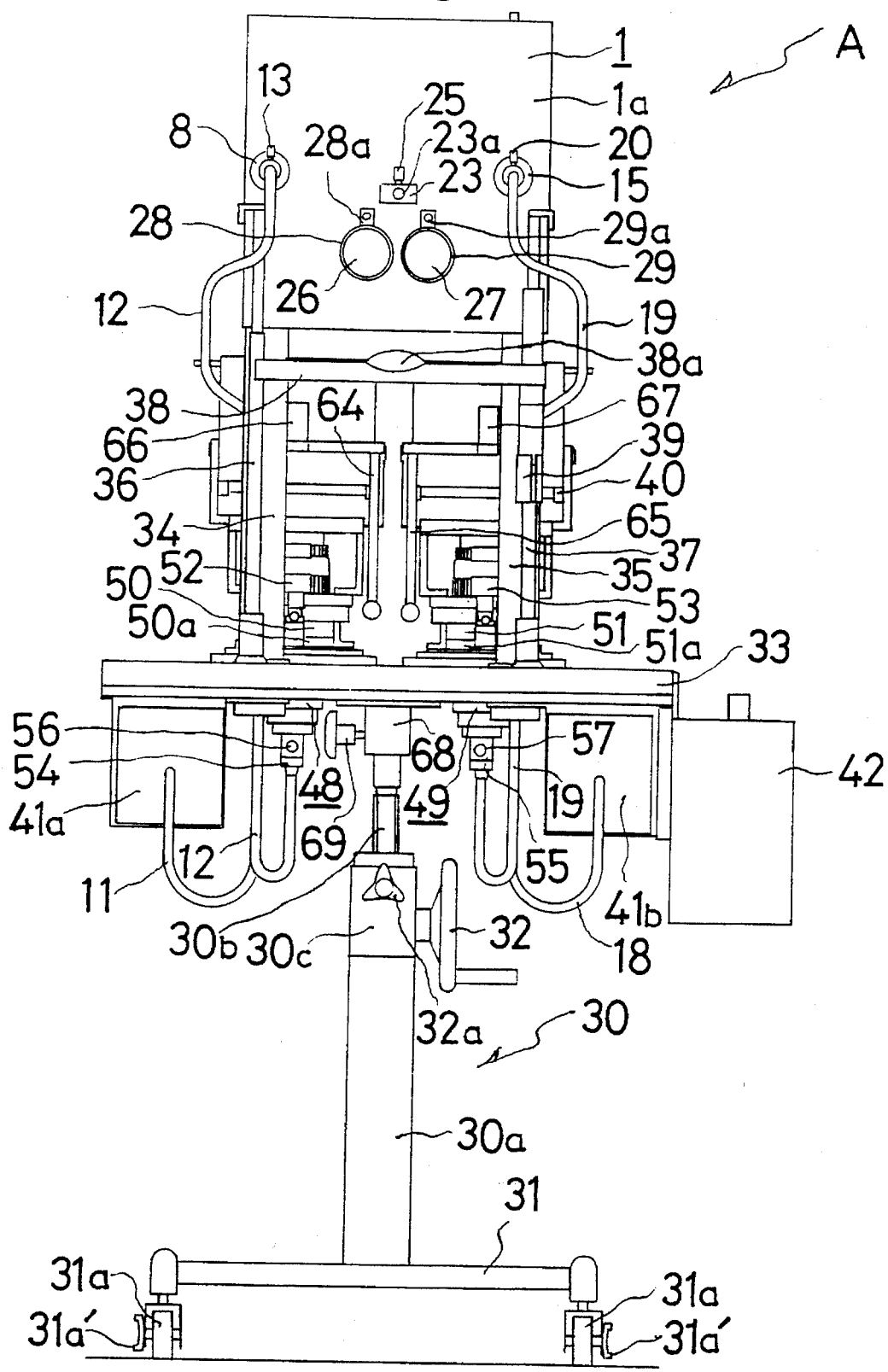
FIG. 1 is a front view showing a phase-contrast haploscope according to a first embodiment of the present invention.
Figure 2:
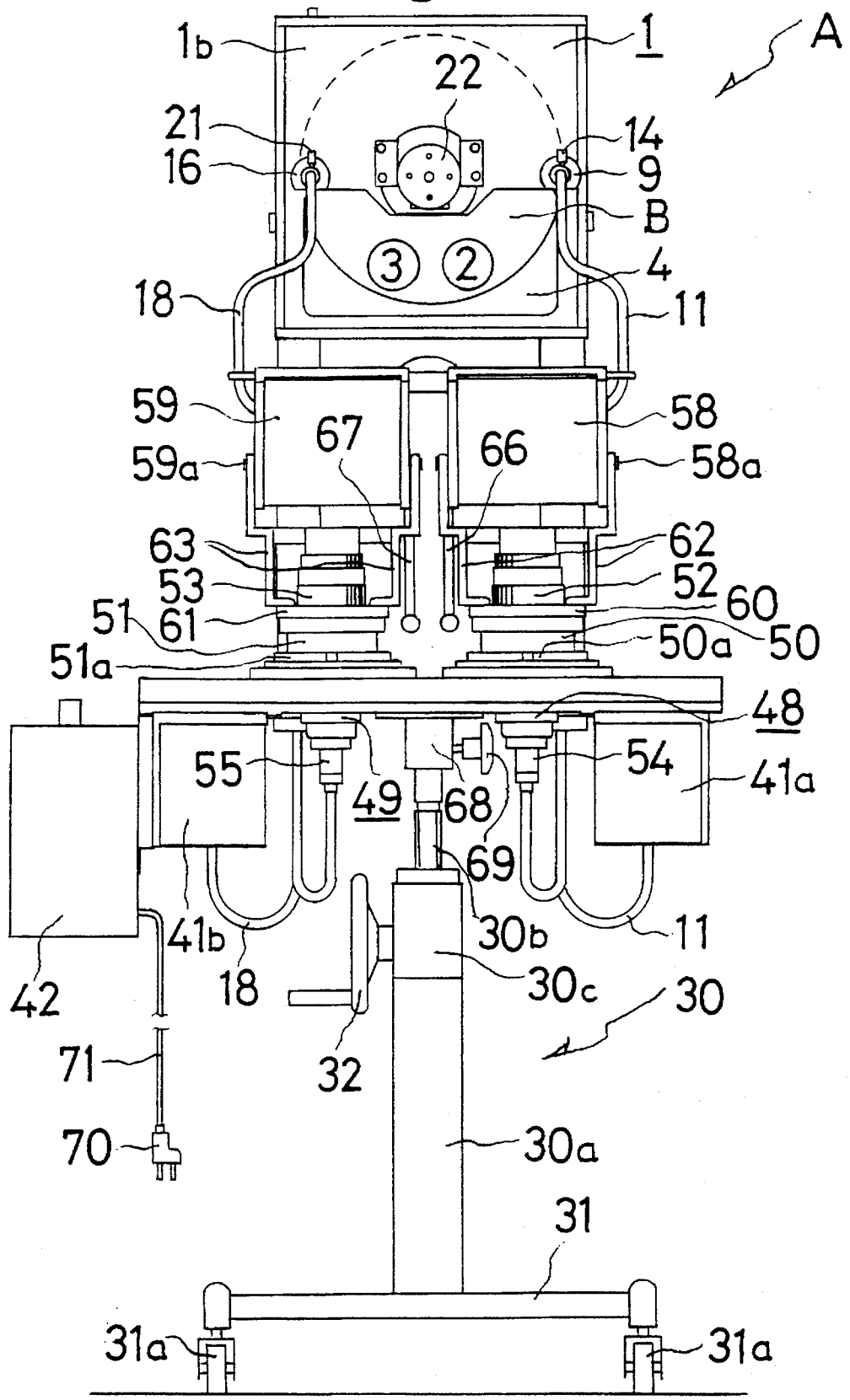
FIG. 2 is a rear view of the haploscope according to the first embodiment.
Figure 3:
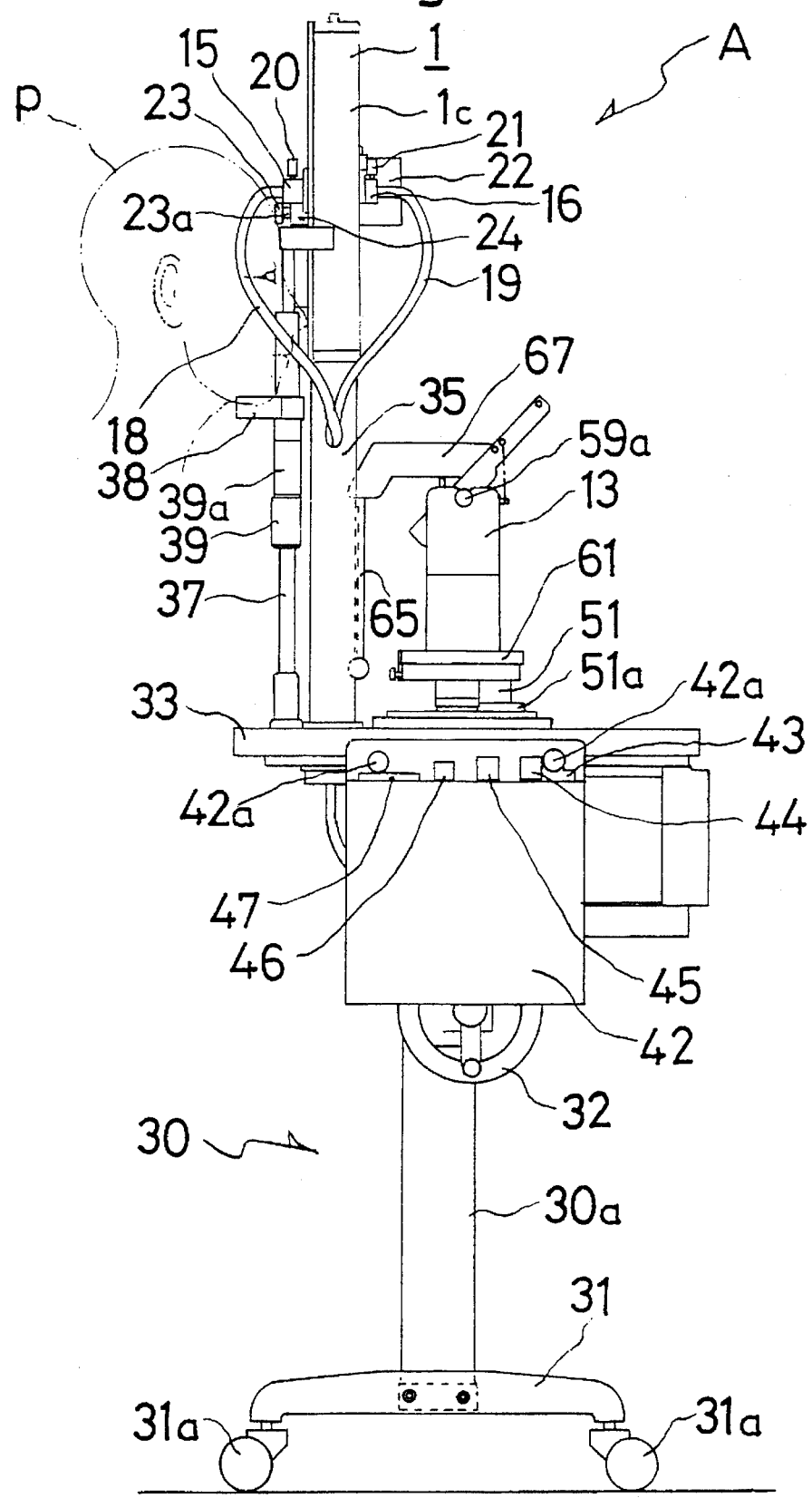
FIG. 3 is a right-hand side view of the haploscope according to the first embodiment.
Figure 7:
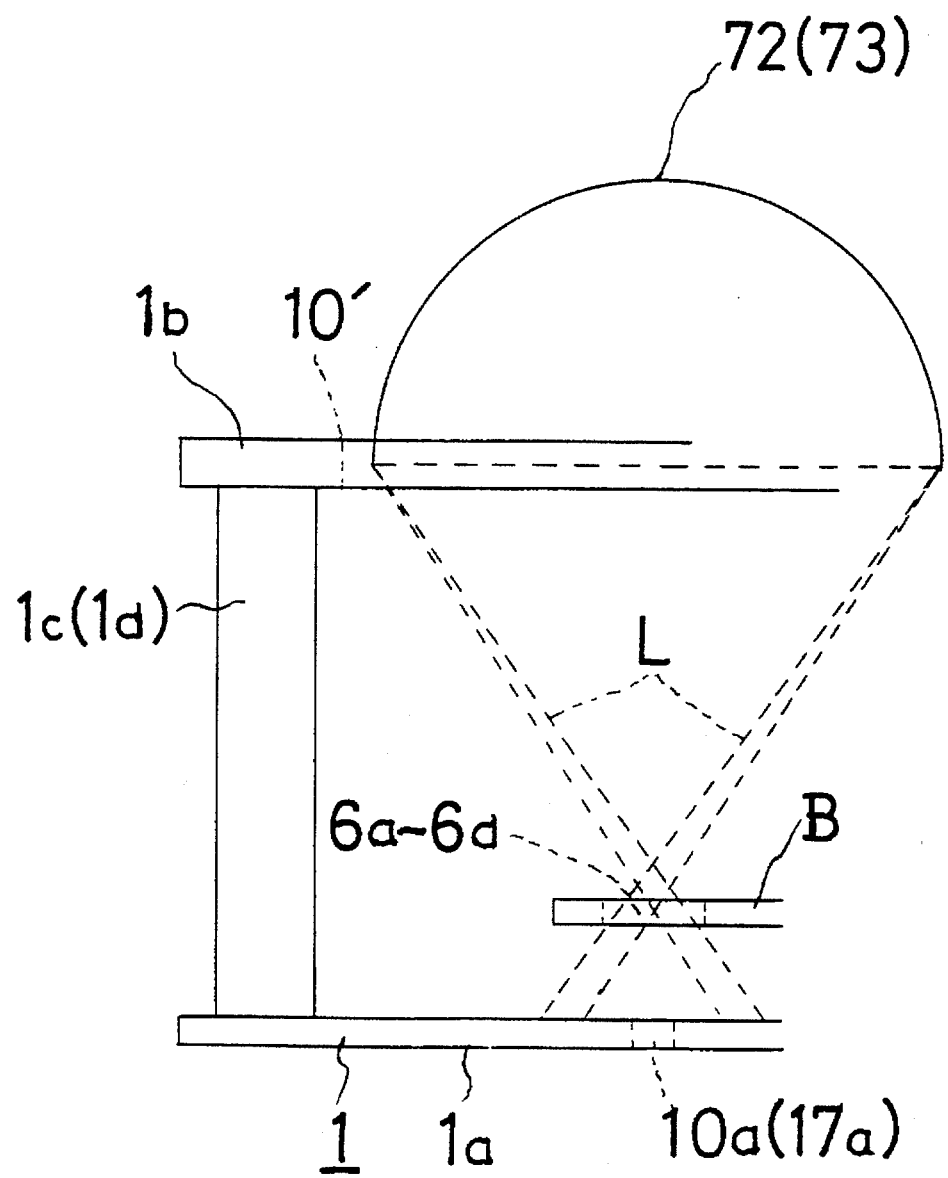
FIG. 7 is a view showing a case where a halogen lamp is attached to a beam emitting hole formed in the rear plate of the disc case.
Figure 8:
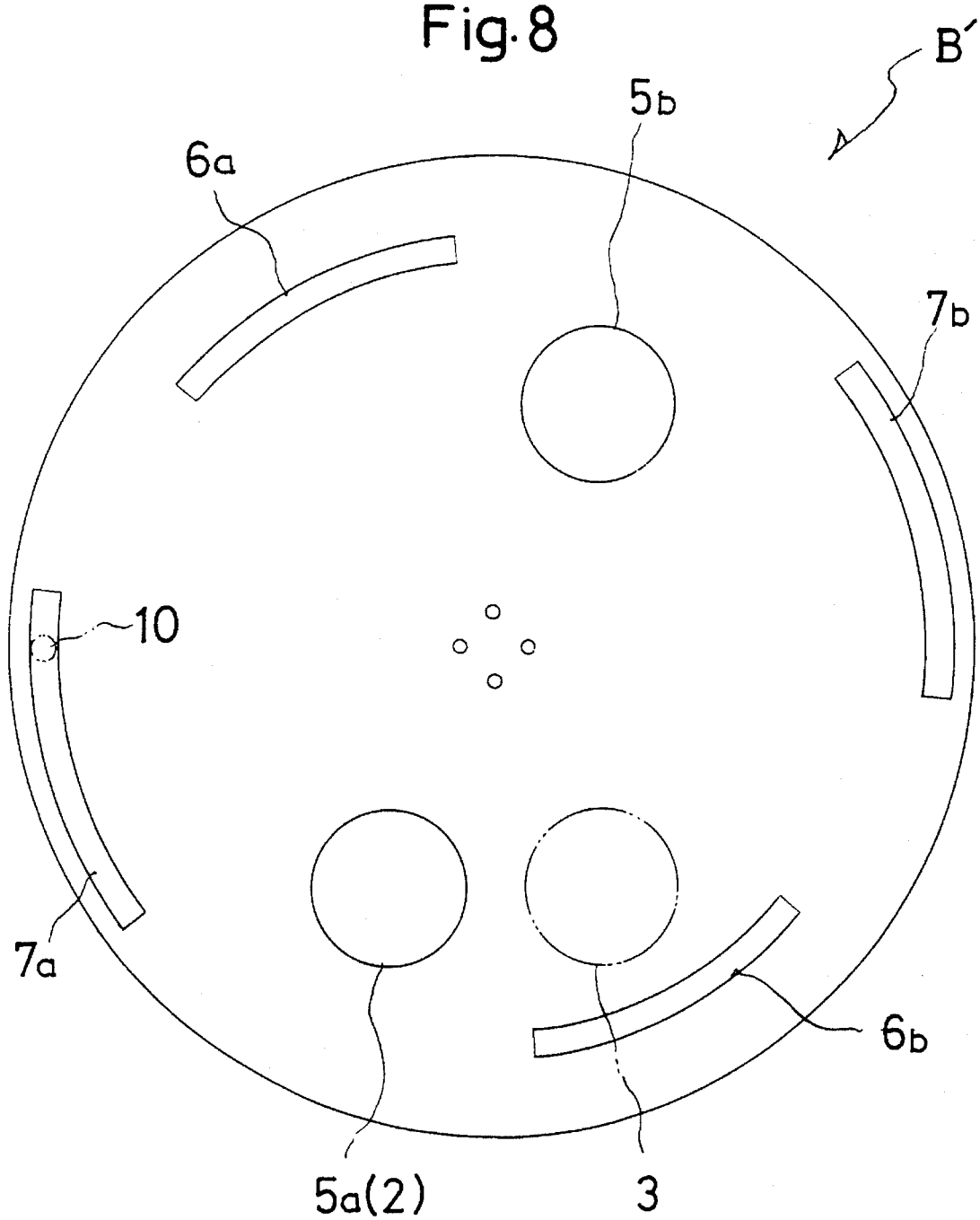
FIG. 8 is an enlarged front view showing another embodiment of a rotary disc according to the present invention.
Figure 9:
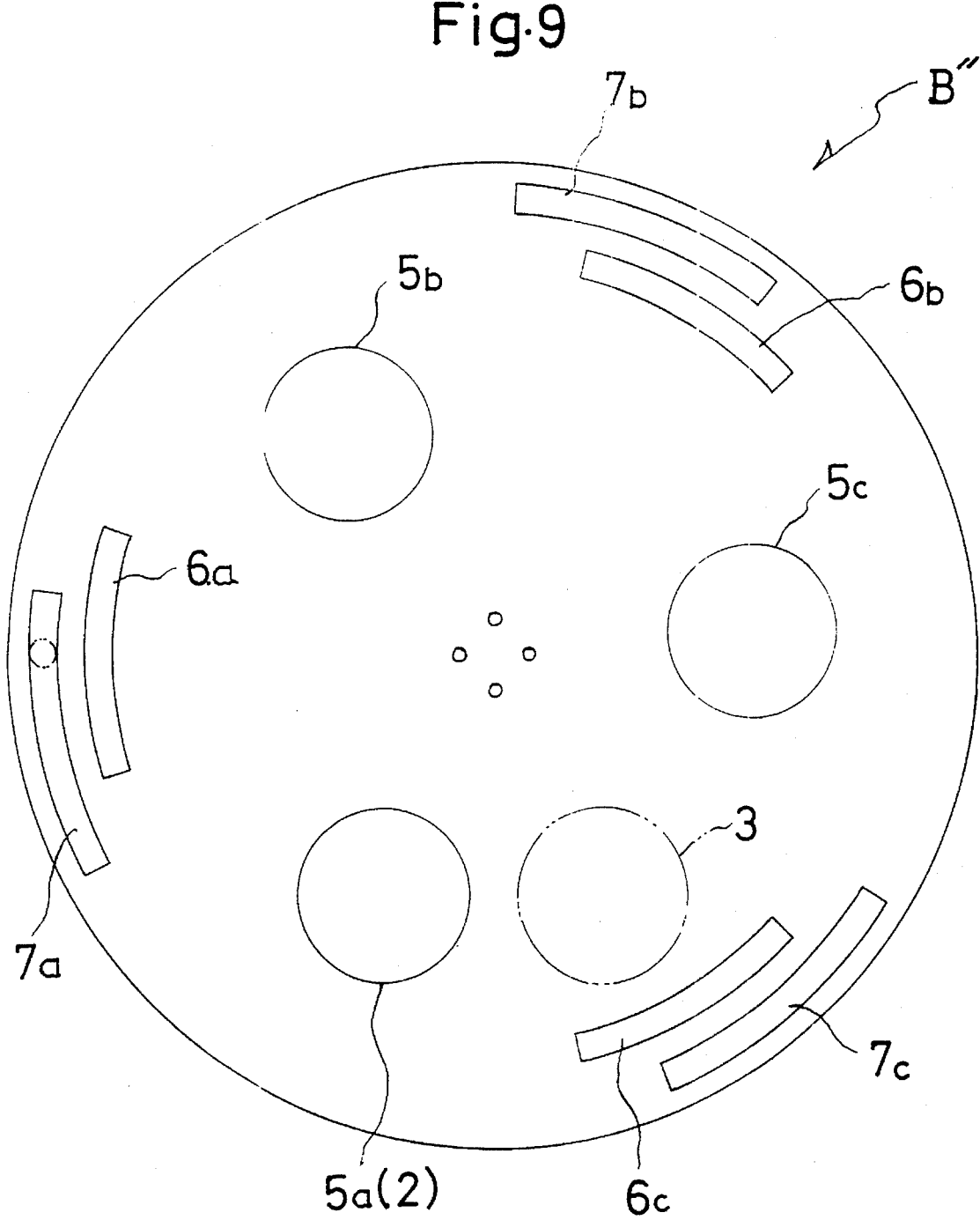
FIG. 9 is an enlarged front view showing still another embodiment of a rotary disc according to the present invention.

FIG. 1 is a front view showing a phase-contrast haploscope according to the present embodiment. FIG. 2 is a rear view showing the haploscope. FIG. 3 is a right-hand side view showing the haploscope. FIG. 4 is a plan view showing a control box. FIG. 5 is an enlarged front view showing a rotary disc of the present embodiment. FIG. 6 is a partially omitted perspective front view showing a disc case with its stationary front plate removed. FIG. 7 is an enlarged plan view of essential portions of the disc case with its top plate removed when a halogen lamp is attached into a left-hand beam emitting hole. FIGS. 8 and 9 are enlarged plan views showing other examples of a rotary disc.

In the figures, reference symbol A denotes a phase-contrast haploscope according to the present embodiment. B, B' and B" denote rotary discs used in the present embodiment. Reference numeral 1 denotes a disc case. 1a denotes a front plate, 1b denotes a rear plate, and 1c and 1d denote right- and left-hand side plates. Designators 2 and 3 denote a pair of circular left- and right-hand look-through holes which face left and right eyes, respectively, and which are formed in the front plate 1a at the center of its lower half portion. Designators 4 denotes a through window provided in the rear plate 1b at the lower half portion thereof.

Designators 5a–5d denote through holes which have the same diameter as the left- and right-hand look-through holes 2, 3 and which are formed in the rotary disc B on concentric circular path α equally spaced at 90 degrees. Designators 6a–6d denote rectangular arc-shaped inner project-through holes which correspond to the left-hand look-through hole 2 and which are formed in the rotary disc B on concentric circular path γ equally spaced at 90 degrees. Designators 7a–7d denote rectangular arc-shaped outer project-through holes which correspond to the right-hand look-through hole 3 and which are formed in the rotary disc B on concentric circular path β equally spaced at 90 degrees.

Designators 8 and 9 denote left-hand connectors which are coaxially mounted to a left-hand beam incident hole 10a and a left-hand beam emitting hole 10 at their outer ends. The holes 10a and 10 are formed in the front plate 1a and rear plate 1b at opposed positions where the holes face on one of inner project-through holes 6a–6d when one of through holes 5a–5d instantaneously coincides with the left look-through hole 2. The beam emitting end of a left-hand optical fiber 11 and the beam incident end of the left-hand transmitting optical fiber 12 are inserted into the left-hand connectors 8, 9 and fixed thereto with set screws 13, 14.

Designators 15 and 16 denote right-hand connectors which are coaxially mounted to a right-hand beam incident hole 17a and a right-hand beam emitting hole 17 at their outer ends. The holes 17a and 17 are formed in the front plate 1a and rear plate 1b at opposed positions where the holes face on one of outer project-through holes 7a–7d when one of through holes 5a–5d instantaneously coincides with the right look-through hole 3. The beam emitting end of a right-hand optical fiber 18 and the beam incident end of a right-hand transmitting optical fiber 19 are inserted into the right-hand connectors 15, 16 and fixed thereto with set screws 20, 21. Reference Designator 22 denotes a variable speed motor mounted on the rear plate 1b at its center. The end of a motor shaft 22a extending through the rear plate 1b is fixed to the rotary disc B at its center.

Reference Designator 23 denotes a forehead rest attached to a slide rod 23a which is inserted into a guide cylinder 24 mounted on the front plate 1a above the middle between the left- and right-hand look-through holes 2, 3. The slide rod 23a as an unillustrated guide groove extending along its upper edge, and the tip end of an adjusting set screw 25 is engaged with the guide groove for fixing. Designators 26 and 27 denote glass or plastic transparent plates stuck on left- and right-hand cylindrical frames 28, 29 whose stoppers 28a, 29a are mounted to the outer ends of the left- and right-hand look-through holes 2, 3, respectively.

Designator 30 denotes a lift support standing upright at the center of a horizontally H-shaped base frame 31 equipped with casters 31a which can be locked. Designator 30a denotes a cylindrical support. 30b denotes a screw rod. 30c denotes a head portion which contains a known adjusting mechanism for raising and lowering the screw rod 30b inserted thereinto by turning a rotary handle 32 in a forward or reverse direction. Designator 32a denotes an adjusting stopper screw for fixing the screw rod 30b at an adjusted position.

Reference designator 33 denotes a table type base and 34 and 35 denote left- and right-hand parallel support stands standing upright on the base 33 to support the disc case 1 thereon. Designators 36 and 37 denote left- and right-hand parallel uprights standing in front of the left- and right-hand parallel support stands 34, 35. Designator 38 denotes a cross-plate which bears a chin rest 38a at its central portion corresponding to the middle between the left- and right-hand look-through holes 2, 3 and which stretches between the left- and right-hand parallel guide uprights 36, 37 in such a manner that its both ends slide up and down along the uprights. Designator 39 denotes a cylindrical slider which is slidably fit onto the right-hand guide upright and which is fixed at an adjusted position with an adjusting set screw 40 in order to position the cross-plate 38 via a sleeve 39a.

Designators 41a and 41b denote left- and right-hand light source boxes which are mounted on the bottom face of the base 33 at both sides thereof and to which beam incident ends of the left- and right-hand optical fibers 11, 18 are connected. Designator 42 denotes a control box attached to the right-hand end of the base 33 in a hanging manner with set screws 42a. Designators 43, 44, 45, 46 and 47 denote a main switch, a right-hand bright control, a left-hand bright control, a speed control, and a digital speedometer, respectively, arranged on a control panel 42b.

Designators 48 and 49 denote a pair of left- and right-hand projectors which upward penetrate the base 33 with a predetermined spacing. Designators 50 and 51 denote left- and right-hand slide loaders which are incorporated into the left- and right-hand projectors 48, 49, respectively, at their top portions and which allow lantern slides n, o to be loaded thereinto or unloaded therefrom. Designators 52 and 53 denote a pair of left- and right-hand zooms which are mounted on the left- and right-hand projectors 48, 49, respectively, at their top ends. Designators 54 and 55 denote left- and right-hand connectors which are connected to the left- and right-hand projectors 48, 49, respectively, at their bottom ends and into which the beam irradiating ends of the left- and right-hand transmitting optical fibers 12, 19 are inserted and fixed with set screws 56, 57.

Designators 58 and 59 denote a pair of left- and right-hand mirrors which are pivotally mounted in left-hand forked brackets 62 and right-hand forked brackets 63 with pivots 58a, 59a in such a manner that a vertical angle can be adjusted and set as desired and as to face the top ends of the left- and right-hand zooms 52, 53. The left- and right-hand forked brackets 62, 63 stand upright on the left- and right-hand seat rings 60, 61, respectively. The left- and right-hand seat rings 60, 61 are mounted rotatably on the top ends of the left- and right-hand projectors 48, 49 in such a manner as to cover the lower portions of the left- and right-hand zooms 52, 53. Designators 64 and 65 denote a pair of left- and right-hand right-angle handles for swinging the left- and right-hand mirrors 58, 59 horizontally and vertically. The handles 64, 65 are fixed to the inner neighboring sides of the left- and right-hand arms 66, 67 which obliquely downwardly project from and are located at the middle portions of the back surfaces of the left- and right-hand mirrors 58, 59.

Designator 68 denotes a screw rod mounting hardware which is mounted on the bottom face of the base 33 at its center and into which the top end of the screw rod 30b is inserted to be fixed with a stopper screw 69. Designator 70 denotes a plug attached to the end of a power cord 71 extending from the control box 42.

As illustrated with a dash-and-two dots line in FIG. 6 and shown in FIG. 7, the left- and right-hand beam emitting holes 10, 17 in the rear plate 1b may be enlarged to obtain left- and right-hand beam emitting holes 10', 17' having a larger diameter, and left- and right-hand halogen lamps 72, 73 may be inserted thereinto for attachment. In this case, electric cords (not shown) in place of the left- and right-hand optical fibers 11, 18 are directly connected to the control box 42, and the left- and right-hand light source boxes 41a, 41b become unnecessary.

In the phase-contrast haploscope A according to the present embodiment described above, four holes of each kind, i.e. through holes 5a–5d and rectangular arc-shaped project-through holes 6a–6d and 7a–7d are arranged with an inter-hole phase angle of 90. The number of holes of each kind is not limited to 4. One hole may be provided, or multiple holes may be arranged at the same phase angle.

In detail, in the rotary disc B for the phase-contrast haploscope according to the present invention, four holes of each kind, i.e. through holes 5a–5d and project-through holes 6a–6d and 7a–7d are arranged. A rotary disc having a single hole of each kind arranged with an inter-hole angle of 360 degrees, rotary disc B' having two holes of each kind arranged with an inter-hole angle of 180 degrees as shown in FIG. 8, and rotary disc B" having three holes of each kind arranged with an inter-hole angle of 120 degrees as shown in FIG. 9 may be acceptable.

In these cases, when the motor 22 coupled directly with the motor shaft 22a rotates at a speed of 120 c/s or 7200 rpm, the changeover speed is calculated as follows:

| | |
|---|---|
| 1 hole | 7200 times/minute |
| 2 holes | 7200 × 2 = 14400 times/minute |
| 3 holes | 7200 × 3 = 21600 times/minute |
| 4 holes | 7200 × 4 = 28800 times/minute |

Hence, to attain the same changeover speed,

| | |
|---|---|
| 1 hole | 7200 rpm |
| 2 holes | 7200/2 rpm = 3600 rpm |
| 3 holes | 7200/3 rpm = 2400 rpm |
| 4 holes | 7200/4 rpm = 1800 rpm |

Thus, as the number of holes increases, the speed of the motor can be lowered. Accordingly, a torque load can be reduced, and a cheaper motor can be employed.

Of course, in place of one large through hole 4 in the present embodiment, a pair of left- and right-hand through holes corresponding to the left- and right-hand look-through holes 2, 3 may be used.

The present embodiment has the above-described concrete structure. Operations of the present embodiment will now be described.

The apparatus according to the present embodiment is moved to a desired place. The apparatus is locked using the locks 31a' of a group of casters 31a. The plug 70 of the power cord 71 is inserted into a power connector (not shown).

After loosening the adjusting stopper screw 32a, the rotary handle 32 is turned in the forward or reverse direction to project or retract the screw rod 30b according to the sitting height of examinee p who sits on a separately prepared chair, so that an appropriate height is attained. The adjusting stopper screw 32a is thereafter tightened.

According to the face profile of the examinee p, after loosening the adjusting set screw 25, the forehead rest 23 is advanced or retracted along the guide cylinder 24 until an appropriate position is reached, and the adjusting set screw 25 is then tightened. Also, after loosening the adjusting set screw 40, the cylindrical slider 39 is vertically slid along the left- and right-side parallel guide uprights 36, 37 until the chin rest 38a together with the cross-plate 38 reaches an appropriate position, and the adjusting set screw 40 is then tightened, thus determining the height of the chin rest 38a.

Thus, the face of the examinee p with respect to the front plate 1a is set so that both eyes of the examinee p are properly seen from the central portions of the left- and right-hand transparent plates 26, 27 of the left- and right-hand look-through holes 2, 3.

After turning on the power switch 43 on the control panel 42b, the left- and right-hand brightness controls 44, 45 are adjusted, and the speed controller 46 is adjusted while checking a speed displayed on the digital speedometer 47.

Next, the left- and right-hand slide boxes 50a, 51a are pulled out, and the left- and right-hand lantern slides n, o used for an examination are loaded thereinto. The slide boxes are inserted back into the left- and right-hand slide loaders 50, 51. The handles 64, 65 for swinging the left- and right-hand mirrors are operated horizontally and vertically so that for example, the targets h, g: on the left- and right-hand lantern slides are projected ion the plane of projection m at a desired position. At the same time, the left- and right-hand zooms 52, 53 are operated to zoom in or out the projected left- and right-hand targets h, g.

After the adjusting operations: have been completed, when the rotary disc B is rotated, for example, at a speed higher than the critical fusion frequency (100–120 c/s or higher) as in the conventional phase-contrast haploscope, the left and right changeover speed becomes twice that of the conventional synchronous type phase-contrast haploscope.

As the rotary disc B rotates at a high speed in the direction of an arrow as illustrated, the centers of the through holes 5a–5d revolve traveling along out the concentric circular path α. The through holes 5a–5d pass one by one in front of the left- and right-hand look through holes 2, 3 whose centers are located on the concentric circular path α. One of the through holes 5a–5d coincides instantaneously with the left-hand look-through hole 2, and then after the elapse of a predetermined instantaneous time, it coincides instantaneously with the right-hand look-through hole 3.

Thus, as a result of the through holes 5a–5d in the rotary disc B revolving counterclockwise and passing in front of the left- and right-hand look-through holes 2, 3, the left- and right-hand look-through holes 2, 3 alternately coincide with one of the through holes. While the rotary disc B makes one rotation, the alternation occurs 4 times for instantaneous coincidence.

In synchronism with the above, as the rotary disc B rotates, the rectangular arc-shaped inner project-through holes 6a–6d and the rectangular arc-shaped outer project-through holes 7a–7d rotate between the left-hand beam emitting end of the left-hand optical fiber 11 or the left-hand halogen lamp 72 and the beam incident end opposed thereto of the beam incident hole of the left-hand transmitting optical fiber 12 on the front plate 1a or between the right-hand beam emitting end of the right-hand optical fiber 18 or the right-hand halogen lamp 72 and the beam incident end opposed thereto of the beam incident hole 17a (not shown) of the right-hand transmitting optical fiber 19 on the front plate 1a, and travel along the inner concentric circular path γ and the outer concentric circular path β, respectively.

Synchronously with the instantaneous coincidence of one of the through holes 5a–5d with the left-hand look-through hole 2, one of the rectangular arc-shaped inner project-through holes 6a–6d corresponding to the one of the through holes 5a–5d passes between the beam emitting end of the left-hand optical fiber 11 or the left-hand halogen lamp 72 and the beam incident end opposed thereto of the left-hand transmitting optical fiber 12.

At that time, a left-hand projecting beam L emitted from the beam emitting end of the left-hand optical fiber 11 or the left-hand halogen lamp 72 passes through one of the rectangular arc-shaped inner project-through holes 6a–6d and enters the beam incident end opposed thereto of the left-hand transmitting optical fiber 12. The beam irradiates the lantern slide n inserted into the left-hand projector 48 via the left-hand transmitting optical fiber 12. The beam from the left-hand projector passes through the left-hand zoom 52. Then, a projecting beam q reflected on the left-hand mirror 58 projects the left-eye target h on the plane of projection m. Thus, the left eye can visually recognize the left-eye target h through the left-hand look-through hole 2 and one of the through holes 5a–5d coinciding instantaneously therewith and the through window 4.

On the other hand, synchronously with the instantaneous coincidence of one of the through holes 5a–5d with the right-hand look-through hole 3, one of the rectangular arc-shaped outer project-through holes 7a–7d corresponding to the one of the through holes 5a–5d passes between the beam emitting end of the right-hand optical fiber 18 or the right-hand halogen lamp 73 and the beam incident end opposed thereto of the right-hand transmitting optical fiber 19.

At that time, a right-hand projecting beam L emitted from the beam emitting end of the right-hand optical fiber 18 or the right-hand halogen lamp 73 passes through one of the rectangular arc-shaped outer project-through holes 7a–7d and enters the beam incident end opposed thereto of the right-hand transmitting optical fiber 19 of the right-hand beam incident hole. The beam irradiates the right-hand lantern slide o inserted into the projector 49 via the right-hand transmitting optical fiber 19. The beam from the projector 49 passes through the right-hand zoom 53. Then, a projecting beam r reflected on the right-hand mirror 59 projects the right-eye target g on the plane of projection m. Thus, the right eye can visually recognize the right-eye target g through the right-hand look-through hole 3 and one of the through holes 5a–5d coinciding instantaneously therewith and the through window 4.

Thus, the left- and right-hand projecting beams L are intermittently blocked as the rotary disc B rotates. Also, synchronously with the coincidence between the left- or right-hand look-through hole 2, 3 and one of the through holes 5a–5d, the targets h and g of the left and right eyes can be alternately changed over at a high speed and separated completely from each other. An examiner such as a doctor adjusts the orientation of the left- and right-hand mirrors 58, 59 and examines in a third party's manner or objectively various binocular functions including the state of fusing the targets h, g in the vertical and horizontal directions.

A second embodiment of the present invention will now be described with reference to drawings.

Figure 10:
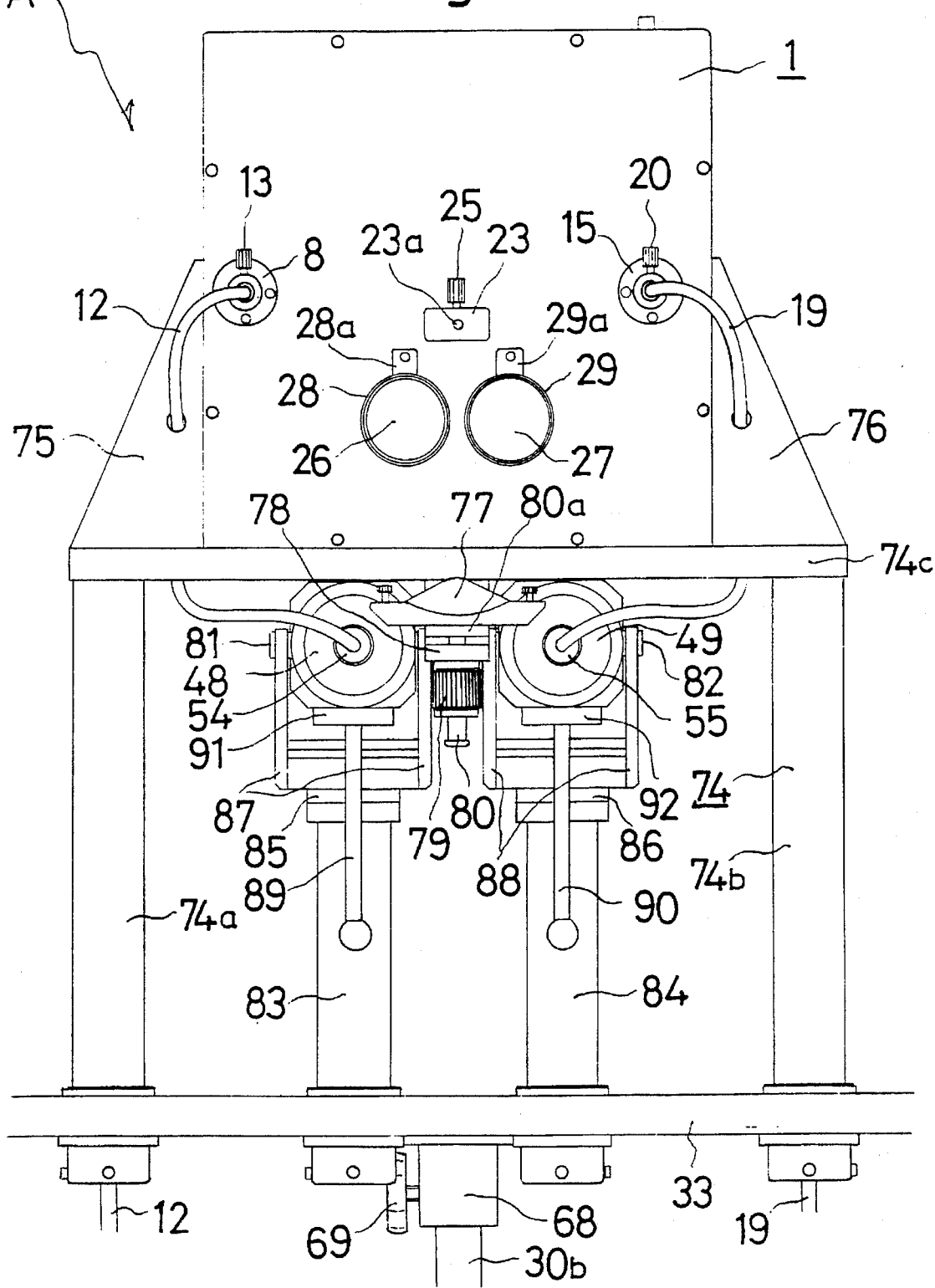
FIG. 10 is a front view showing essential portions of a phase-contrast haploscope according to a second embodiment of the present invention.
Figure 11:
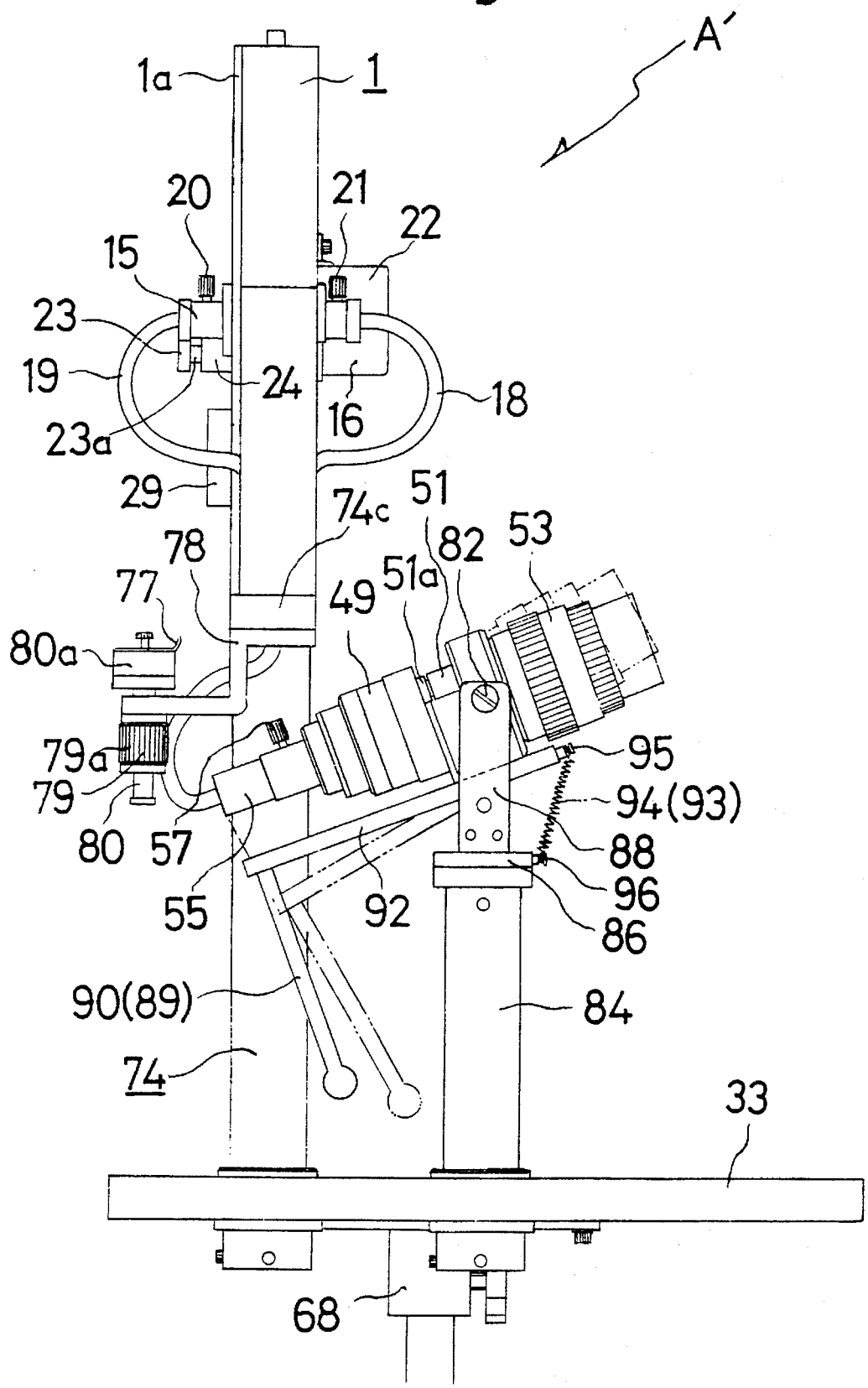
FIG. 11 is a right-hand side view showing essential portions of the haploscope according to the second embodiment.
Figure 12:
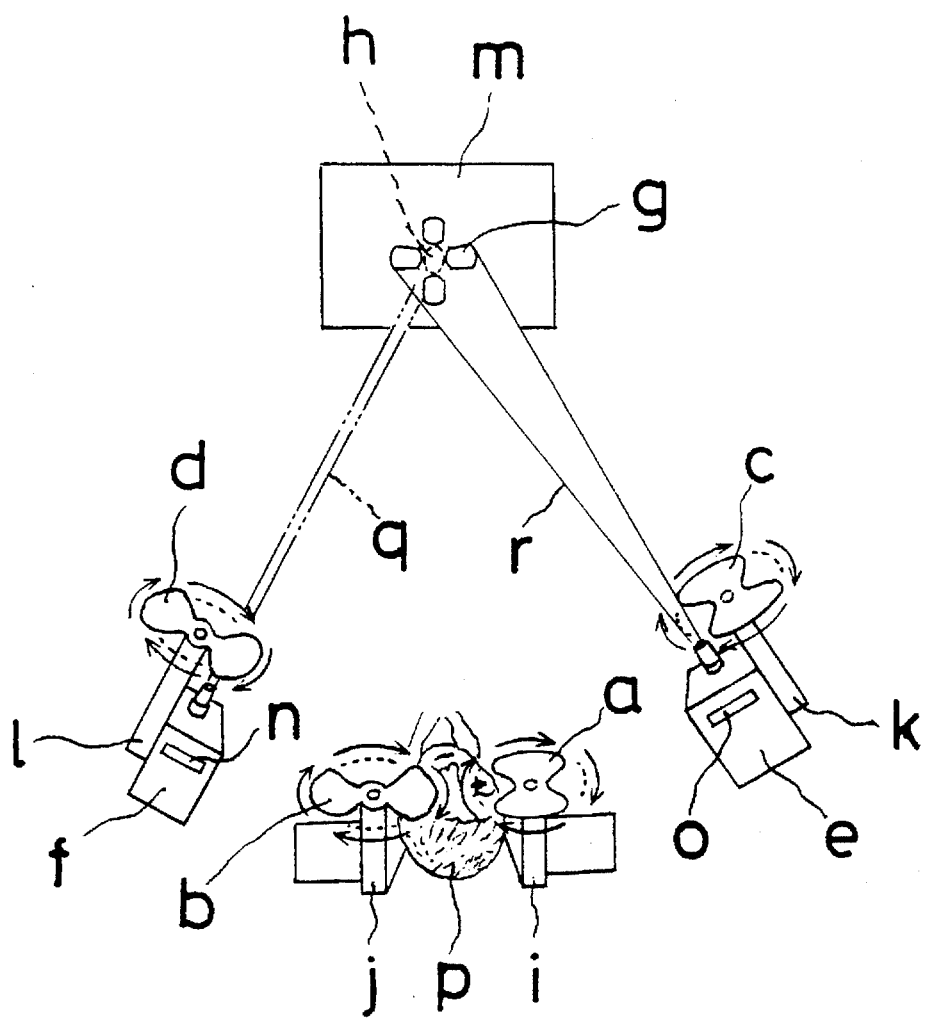
FIG. 12 is an explanatory illustration showing examination with a synchronous type phase-contrast haploscope according to the prior art.

FIG. 10 is a front view showing essential portions of a phase-contrast haploscope according to the present embodiment. FIG. 11 is a right-hand side view of the haploscope. The same members as the first embodiment are denoted by the same reference numbers to avoid redundant description.

In the figures, A' denotes the phase-contrast haploscope according to the present embodiment. Designator 74 denotes a gantry stand which comprises left- and right-hand supports 74a, 74b standing upright on a base 33 to pass the intermediate portions of left- and right-hand optical fibers 11, 18 therethrough and a top plate 74c. Designators 75 and 76 denote left- and right-hand right-angled triangle shaped auxiliary cases which stand on the top plate 74c of the gantry stand 74 on both sides of a disc case 1 standing on the top plate 74c in such a manner as to support the sides of the disc case and which allow the intermediate portions of the left- and right-hand optical fibers 11, 18 and left- and right-hand transmitting optical fibers 12, 19 to pass therethrough for neat arrangement.

Designator 77 denotes a chin rest fixed to a top-end head 80a of a screw rod 80 which passes through the end portion of a stepped crank bracket 78, whose base end is fixed on the bottom face of the top plate 74c of the gantry stand 74 below the middle between left- and right-hand look-through holes 2, 3, and which rises or lowers by turning a cylindrical adjusting nut 79 having knurls 79a and engaging therewith.

Designators 81 and 82 denote left- and right-hand pivoting pins which pivot the left- and right-hand projectors 50, 51 in a vertically swinging manner between left-hand forked brackets 87 and between right-hand forked brackets 88, respectively. The left- and right-hand forked brackets 87, 88 stand on forked bracket base coupling portions 85, 86, respectively, in a horizontally rotatable manner, which coupling portions are located on the top ends of left- and right-hand support stands 83, 84 studded upright into a base 33.

Designators 89 and 90 denote a pair of handles, as operating means, projecting downward at right angles to auxiliary plates 91, 92 at their rear ends, which auxiliary plates are attached to the bottom portions of slide loaders 50, 51 of left- and right-hand projectors 48, 49.

Designators 93 and 94 denote equilibrating tension springs one end of which is attached to the end of the left- or right-hand auxiliary plate 91, 92 with a retaining pin 95 and the other end of which is attached to the forked bracket base coupling portion 85, 86 with a retaining pin 96, thereby horizontally biasing the left- and right-hand projectors 48, 49 and the left- and right-hand auxiliary plates 91, 92. Other portions are configured in the same manner as the first embodiment.

The present embodiment has the above-described concrete structure. Operations of the present embodiment will now be described.

While adjusting a forehead rest 23, the vertical position of the chin rest 77 is set according to the face profile of examinee put by turning the cylindrical adjusting nut 79 in the forward or reverse direction to raise or lower the screw rod 80.

Thus, the face of the examinee p is set with respect to the front plate 1a so that both eyes of the examinee p are properly seen from the central portions of the left- and right-hand transparent plates 26, 27 of the left- and right-hand look-through holes 2, 3.

The left- and right-hand handles 89, 90 are moved right and left or up and down to horizontally swing the left- and right-hand forked brackets 87. 88 and at the same time to vertically swing the left- and right-hand projectors 48, 49 so that for example, the left- and right-hand targets h, g on the left- and right-hand lantern slides n, o are projected on the plane of projection m at a desired position. At the same time, operate left- and right-hand zooms 52, 53 to zoom in or out the projected left- and right-hand targets h, g.

Other members and mechanisms are adjusted in the same manner as the first embodiment, and hence various examinations of the examinee p are executed in the same manner.

As described above, a rotary disc according to the present invention provides a higher rotational speed above the critical fusion frequency of a single rotary disc to change over the vision of both right and left eyes and thus to separate targets of both right and left eyes from each other. Hence, it becomes possible to set conditions quite similar to the ordinary vision for both right and left eyes.

Thus, under these conditions, it is possible to examine various functions of binocular vision, i.e. subjective angle of squint, retinal correspondence, fusion faculty, subjective vision, suppression, aniseikonia, circumflex deviation and others in near natural state. Accordingly, it is possible to easily examine an examinee over a long period of time without causing uncomfortableness or pain and thus to obtain a higher diagnostic reliability.

Also, a phase-contrast haploscope according to the present invention allows one to adjust it according to the sitting height and face profile of an examinee irrespective of age or sex, and hence can immediately cope with any examinee. A small-sized, light, compact structure allows the apparatus to be moved to any location for use anywhere a power source and a required occupational space are available. When not in use, the apparatus can be stored in a compact manner.

Moreover, since only one motor is used to rotate a rotary disc, synchronous control is unnecessary, and hence a control technique is quite simple. As a result, the apparatus does not require much adjustment, is reliable, is very durable, and is easy to maintain. Also, no special skills are required for operation, and an initial cost is lower.

The phase-contrast haploscope according to the present invention is equipped with zooms and allows mirrors or projectors themselves to swing horizontally and vertically by handle operations. Thus, left- and right-hand targets projected on the plane of projection can be individually zoomed in or out or moved vertically or horizontally. As a result, it is possible to freely examine various functions of binocular vision, i.e. subjective angle of squint, retinal correspondence, fusion faculty, subjective vision, suppression, aniseikonia, circumflex deviation and others.

By changing over the vision of both right and left eyes at a higher rotational speed above the critical fusion frequency of a single rotary disc and accordingly separating targets of both right and left eyes from each other, it becomes possible to set conditions quite similar to the ordinary vision for both right and left eyes. As a result, examinations can be conducted in near natural state. Accordingly, it is possible to easily examine an examinee over a long period of time without causing uncomfortableness or pain and thus to obtain a higher diagnostic reliability.

Moreover, since as compared with conventional apparatus, the apparatus according to the present invention is smaller in size and scale, is minimized in the number of parts, and uses only one motor, synchronous control is unnecessary, and hence a control technique is quite simple. As a result, the apparatus does not require much adjustment, is reliable, is very durable, and is easy to maintain. Also, no special skills are required for operation, an initial cost is lower, and the apparatus does not occupy much space.

What we claim are:

1. A rotary disc for a phase-contrast haploscope having a rotary disc motor for rotating said rotary disc and a stationary front plate defining first and second light projection path apertures and left- and right-hand look-through holes which are shaped in a circle and which are formed therein at positions corresponding to a subject's left and right eyes, the stationary front plate rotatably supporting said rotary disc and leaving a predetermined clearance between the rotary disc and the stationary front plate, said rotary disk comprising:

a plate member having a substantially circular shape:

said plate member defining through holes which are shaped in a circle having substantially the same size as said left- and right-hand look-through holes and which are formed on a first circular path concentric with a center of said plate member, said through holes being disposed to pass in front of said left- and right-hand look-through holes in sequence at a high rotational speed to instantaneously coincide with one of said left- and right-hand look-through holes at a time:

said plate member defining first project-through holes which are shaped in a rectangular arc and which are formed on a second circular path concentric with said center of said plate member having a different diameter from that of first circular path, said first project-through holes being disposed to pass in front of said first light projection path aperture coincident with alignment of respective ones of said through holes with the left-hand look-through hole: and second project-through holes which are shaped in a rectangular arc and which are formed on a third circular path concentric with the center of said plate member having a different diameter from those of said first and second circular paths, said second project-through holes being disposed to pass in front of said second light projection path aperture coincident with alignment of respective ones of said through holes with the right-hand look-through hole.

2. A rotary disc for a phase-contrast haploscope according to claim 1, wherein the through holes and the first and second project-through holes are formed on and spaced equally apart on the respective circular paths.

3. A rotary disc for a phase-contrast haploscope according to claim 1, wherein the through holes and the first and second project-through holes are respectively arranged with an inter-hole phase difference of 90 degrees in a circumferential direction.

4. A rotary disc for a phase-contrast haploscope according to claim 1, 2 or 3, wherein a target comprises one of a character, a graphic pattern, a symbol, a combination thereof, and other images.

5. A phase-contrast haploscope comprising:

a disc case which has a front plate having a pair of left- and right-hand look-through holes in its lower half portion and a rear plate having left- and right-hand through holes formed in its lower half portion opposing those of said front plate:

a pair of left- and right-hand beam emitting holes and beam incident holes corresponding to the left- and right-hand look-through holes formed respectively in the front plate and in the rear plate at desired opposed positions:

light source means for sourcing light to said left- and right-beam emitting holes:

a motor driven rotary disc rotatably supported between said front and said rear plates;

the rotary disc having through holes and project-through holes formed therein, the through holes and project-through holes sweeping out respective concentric circular paths of different diameters and passing at a high rotational speed respectively between said left- and right-hand look-through holes and said left- and right-hand through holes, and between said left- and right-hand beam emitting holes and said left- and right-hand beam incident holes, in such a manner as to instantaneously coincide with corresponding ones of said left- and right -hand look through holes and said left- and right-hand beam emitting holes: and left- and right-hand projectors having slide loaders allowing a slide to be inserted thereinto and removed therefrom and means for accepting beams from respective ones of said left- and right-hand beam incident holes for irradiating the slides with the beams and projecting beams having passed through said slides onto planes of projection.

6. A phase-contrast haploscope according to claim 5, wherein the disc case and said left- and right-hand projectors are mounted on a base which is raised and lowered for positioning.

7. A phase-contrast haploscope according to claim 6, wherein the disc case is mounted on a gantry stand or left- and right-hand parallel support stands standing on the base, which left- and right-hand parallel support stands are accompanied by left- and right-hand parallel guide uprights standing in front of them.

8. A phase-contrast haploscope according to claim 6 or 7, wherein the base is supported on a mobile lifter support.

9. A phase-contrast haploscope according to claim 5, 6, or 7, wherein a forehead rest is fixed to the end of a slide rod which is slidably inserted into a guide cylinder for positioning and adjustment, said guide cylinder being mounted on the front plate above the middle between the left- and right-hand look-through holes.

10. A phase-contrast haploscope according to claims 5, 6, or 7, wherein a transparent plate is attached onto the left- and right-hand look-through holes by appropriate means.

11. A phase-contrast haploscope according to claim 5, 6 or 7, wherein said light source means includes:

connectors attached to the left- and right-hand beam emitting holes at sides opposite said rotary disc;

light source boxes having light output connectors: and left- and right- hand optical fibers connecting respective ones of said left- and right-hand beam emitting holes to respective ones of said light output connectors.

12. A phase-contrast haploscope according to claim 5, 6 or 7, wherein said light source means includes:

sockets for accepting halogen lamps disposed at the left- and right-hand beam emitting holes project into the left- and right-hand beam emitting holes toward said rotary disc.

13. A phase-contrast haploscope according to claim 5, 6 or 7, wherein said means for accepting beams includes:

connectors attached to the left- and right-hand beam incident holes at their outer ends; and left- and right-hand transmitting optical fibers coupled to the connectors and input ports of said left- and right-hand projectors respectively.

14. A phase-contrast haploscope according to claim 5, 6, or 7, wherein a motor is mounted on the outer face of the rear plate and a motor shaft to which the rotary disc is attached penetrates the rear plate inwardly.

15. A phase-contrast haploscope according to claim 6 or 7, wherein a control box is attached to one end of the base in a hanging manner.

16. A phase-contrast haploscope according to claim 5, 6, or 7, wherein zooms are integrally incorporated into the left- and right-hand projectors at their forward ends.

17. A phase-contrast haploscope according to claim 5, 6 or 7, wherein said means for accepting beams includes:

connectors integrally incorporated into the left- and right-hand projectors at their rear ends: and left- and right-hand transmitting optical fibers coupled to the connectors and output sides of said left- and right-hand beam incident holes respectively.

18. A phase-contrast haploscope according to claim 5, 6, or 7, wherein the left- and right-hand projectors upward penetrate the base with a predetermined spacing.

19. A phase-contrast haploscope according to claims 7, wherein the gantry stand include a chin rest which is fixed in a manner capable of rising or lowering for positioning to the end portion of a crank bracket, whose base end is fixed on the bottom face of the top plate of the gantry stand below the middle between the left- and right-hand look-through holes.

20. A phase-contrast haploscope according to claim 7, wherein the left- and right-hand parallel guide uprights include a cross-plate which bears a chin rest at a central portion thereof aligned beneath a middle between the left- and right-hand look-through holes and the cross-plate is slidably supported by the left- and right-hand parallel guide uprights in such a manner that the cross-plate is slidable up and down along the parallel guide uprights for positioning.

21. A phase-contrast haploscope according to claim 6, wherein each of the left- and right-hand projectors is pivoted between forked brackets in such a manner that a vertical angle is adjustable using operating means of the forked brackets, which forked brackets are mounted on top ends of left- and right-hand support stands standing on the base in such a manner as to be horizontally swingable using the operating means.

22. A phase-contrast haploscope according to claim 21, wherein the left- and right-hand projectors each have:

an equilibriating tension spring with one end attached to an auxiliary plate on a bottom side thereof and another end of said equilibriating tension spring attached to a base of a respective one of said forked brackets to bias said left- and right- projectors in a predetermined position: and a handle attached to the rear end of the auxiliary plate extending downward.

23. A phase-contrast haploscope according to claim 22, wherein said beam accepting means includes left- and right-hand optical fibers transmitting light from said left- and right-hand beam incident holes to said left- and right-hand projectors.

24. A phase-contrast haploscope according to claim 5, wherein the left- and right-hand projectors respectively include:

left- and right-hand zooms:

left- and right-hand seat rings rotatably mounted on the top ends of the projectors in such a manner as to cover left- and right-hand zooms:

forked brackets mounted on the left- and right-hand seat rings to rotate with the seat rings to effect horizontal swing movement of the forked bracket;

left- and right-hand mirrors pivotally mounted in the forked brackets in such a manner that a vertical angle is adjustable by pivoting to effect vertical swing movement; and operating means for effecting horizontal and vertical swing movement of said left- and right-hand mirrors above too ends of the left- and right-hand zooms.

25. A phase-contrast haploscope according to claim 24, wherein the operating means for effecting horizontal and vertical swing movement is a pair of left- and right-hand right-angle handles fixed to inner sides of the left- and right-hand mirrors to obliquely project downward from middle portions of the left- and right-hand mirrors.

26. A phase-contrast haploscope according to claim 25, wherein said beam accepting means includes left- and right-hand optical fibers transmitting light from said left- and right-hand beam incident holes to said left- and right-hand projectors.

27. An apparatus for performing binocular vision examinations upon a subject comprising:

a housing defining left and right viewing apertures disposed to permit substantial alignment with the subject's left and right eyes and permit viewing through said housing;

projection light source means for sourcing light for projection of left and right images;

said housing defining first arid second light source apertures;

guide means for directing light from said projection light source means through said first and second light source apertures;

first and second projection means for projecting images using said light passing through respective ones of said first and second light source apertures;

a rotary disc;

means for rotating said rotary disk within said housing at a position permitting occlusion of said first and second light source apertures and said left and right viewing apertures;

said rotary disc defining at least one viewing aperture disposed to align with said left and right viewing apertures such that only one of said left and right viewing apertures is not occluded by rotation of said rotary disc at a given time; and said rotary disc defining first and second light source transmission apertures disposed to align with respective ones of said first and second light source apertures during rotation of said rotary disc to permit transmission of light therethrough coincident with respective ones of said left and right viewing apertures not being occluded by said rotary disc to permit said first and second projection means to project images viewable only through respective ones of said left and right viewing apertures.

* * * * *

UNITED STATES PATENT OFFICE
CERTIFICATE OF CORRECTION

Patent No. 5,619,290                    Dated  April 8, 1997

Inventor(s) Shigekatsu NAKAYAMA et al.

It is certified that error appears in the above-identified patent and that said Letters Patent is hereby corrected as shown below:

Item [73]
On the Title page, change the Assignee's name from "Tagawa Denki Kenkyusyo Company" to --Tagawa Denki Kenkyusyo Company, Incorporated--.

Signed and Sealed this

Twelfth Day of August, 1997

Attest:

BRUCE LEHMAN

Attesting Officer        Commissioner of Patents and Trademarks